United States Patent [19]
Schmitz et al.

[11] Patent Number: 5,643,623
[45] Date of Patent: Jul. 1, 1997

[54] HEALTH FOOD PRODUCT AND ITS USES

[75] Inventors: Harold H. Schmitz, Hackettstown; Dana L. Michael, Andover, both of N.J.; James C. Neumann, Stroudsburg, Pa.; Michael Webster, Blairstown, N.J.; Elizabeth Zemenek, Easton, Pa.; Ralph Jerome, Blairstown, N.J.

[73] Assignee: Mars Incorporated, McClean, Va.

[21] Appl. No.: 473,451

[22] Filed: Jun. 7, 1995

[51] Int. Cl.$^6$ .................................................. A23L 1/302

[52] U.S. Cl. ..................... 426/73; 426/72; 426/74; 426/311; 426/541; 426/544; 426/648

[58] Field of Search ........................... 426/72, 73, 74, 426/311, 541, 544, 648

[56] References Cited

U.S. PATENT DOCUMENTS

| | | | |
|---|---|---|---|
| 2,538,202 | 1/1951 | Kimball | 426/541 |
| 3,655,406 | 4/1972 | Klaul | 426/250 |
| 4,307,117 | 12/1981 | Leshik . | |
| 4,343,823 | 8/1982 | Todd, Jr. et al. . | |
| 4,451,488 | 5/1984 | Cook et al. . | |
| 4,999,205 | 3/1991 | Todd, Jr. . | |
| 5,077,069 | 12/1991 | Chang et al. | 426/541 |
| 5,084,293 | 1/1992 | Todd, Jr. . | |
| 5,234,702 | 8/1993 | Katz et al. . | |
| 5,266,344 | 11/1993 | Mimura et al. . | |
| 5,290,481 | 3/1994 | Todd, Jr. | 426/541 |
| 5,290,605 | 3/1994 | Shapira . | |
| 5,401,504 | 3/1995 | Das et al. | 424/195.1 |

OTHER PUBLICATIONS

Thomas, J.A. (1994) Oxidative stress, oxidant defense and dietary constituents. In "Modern Health in Nutrition and Disease" (eds. M.E. Shils, J.A. Olson and M. Shike), Lea and Febiger, Philadelphia.

Meydani, M. and Evans, W.J. (1993) Free radicals, exercise and aging. In "Free Radicals in Aging" (ed. B.P. Yu), CRC Press, London.

Halliwell, B. (1994) Free Radicals and Antioxidants: a personal view. Nutr. Rev. 52:253–265.

Schmitz, H.H., Poor, C.L., Gugger, E.T. and Erdman, J.W., Jr. (1993) Analysis of Carotenoids in human and animal tissue. Meth. Enz. 214:102–116.

Vitamins (1991) In "Encyclopedia of food science and technology", parts 1–8, vol. 4, John Wiley and Sons, Inc.

Ziegler, R.G. (1989) A review of epidemiologic evidence that carotenoids reduce the risk of cancer. J. Nutr. 119P:116–122.

Pincemail et al., (1988), "Tocopherol mobilization during intensive exercise", Eur. J. Appl. Physiol. 57:189–191.

Smith, L.L., (1990) "Acute inflammation: the underlying mechanism in delayed onset muscle soreness?" American College of Sports Medicine vol. 23, No. 5, pp. 542–551.

Novelli, G.P., Bracciotti, G., and Falsini, S., (1990) "Spin-trappers and vitamin E prolong endurance o muscle fatigue in mice" Free Rad. Biol. Med. 8:9–13.

(List continued on next page.)

*Primary Examiner*—Helen Pratt
*Attorney, Agent, or Firm*—Curtis, Morris & Safford, P.C.

[57] ABSTRACT

A health food product containing a first component in the form of a discrete portion from a second component provides enhanced in vivo oxidative defense indices and prevents or attenuates exercise-induced in vivo oxidative stress as indicated by cellular and/or tissue modification. The first component includes an antioxidant mixture containing a blend of antioxidants selected from all-trans beta-carotene, a mixture of cis beta-carotenes, all-trans alpha-carotene, a mixture of cis alpha-carotenes, all-trans lycopene, a mixture of cis lycopenes, all-trans gamma-carotene, a mixture of cis gamma-carotenes, zeta-carotene, phytofluene, phytoene, vitamin C, vitamin E and curcumin. Internalization and integration of the above nutrients within a lipid containing core of the food product facilitates absorption of the fat-soluble components in the gastrointestinal tract following consumption, increases shelf-life and minimizes degradation of these labile compounds by minimizing exposure to heat, light and/or oxygen, and prevents disadvantageous yellow/orange coloration of the outer material of the food product.

25 Claims, 1 Drawing Sheet

OTHER PUBLICATIONS

Jackson, M.J. and O'Farrell, S. (1993) "Free radicals and muscle damage" British Medical Bulletin vol. 49, No. 3 pp. 630–641.

Meydani et al., (1990) "Protective effect of vitamin E on exercise-induced oxidative damage in young and older adults" Free Rad. Biol. Med. 9(Suppl 1): 109.

Sumida, et al., (1989) "Exercise-induced lipid peroxidation and leakage of enzymes before and after vitamin E supplemention" Int. J. Biochem. vol. 21, No. 8, pp. 835–838.

Gohil, et al., (1986), "Vitamin E deficiency and vitamin C supplements: exercise and mitrochondrial oxidation" The American Physiological Society.

Meydani, et al., (1992) "Antioxidant response to exercise-induced oxidative stress and protection by vitamin E" Ann. N.Y. Acad. Sci. 669:363–4.

Cannon, et al., (1991) "Acute phase response in exercise. II. Associations between vitamin E, cytokines, and muscle proteolysis" The American Physiological Society R1234.

Duthie, et al., (1990) "Blood antioxidant status and erythrocyte lipid peroxidation following distance running" Archives of Biochemistry and Biophysics, vol. 282, No. 1, pp. 78–83.

Singh, V., (1992) "A current perspective on nutrition and exercise" J. Nutr. 122: pp. 760–765.

Witt, E.H., Reznick, A.Z., Viguie, C.A., Starke-Reed, P., and Packer L., (1992) "Exercise, oxidative damage and effects of antioxidant manipulation" J. Nutr. 122: pp. 766–773.

Tiidus, P.M., and Houston, M.E., (1994) "Antioxidant and oxidative enzyme adaptations to vitamin E deprivation and training" Medicine and Science in Sports and Exercise, vol. 26, No. 3, pp. 354–359.

Sejersted, O.M. and Westgaard, R.H. (1988) Editorial "Occupational muscle pain and injury; scientific challenge" Eur. J. Appl. Physiol. 57:271–274.

J.E. Kinsella, (1981) "Dietary fat and prostaglandins: possible beneficial relationships between food processing and public health" Food Technology, pp. 89–98.

Sarah Rabkin, S., (Jun., 1994) Drugs "Why Ibuprofen's bigger than Aspirin" Hippocrates, p. 20.

Walsh, J., (May/Jun. 1994) "The morning after", Women's Sports & Fitness, p. 74.

Newham, D.J., (1988) "The consequences of eccentric contractions and their relationship to delayed onset muscle pain" Eur. J. Appl. Physiol. 57: 353–359.

Product information by Quest International on Tumeric Extract 955.

Toonesen, H.H., (1992) American Chemical Society, Symposium Series 507, Chapter 11 "Chemistry of Cursumin and Curcuminoids".

Huang, et al., (1991) "Inhibitory effects of curcumin on in vitro lipoxygenase and cyclooxygenase activities in mouse epidermis" Cancer Research vol. 51, pp. 813–819.

Mukhopadhyay, et al., (1982) "Anti-inflammatory and irritant activities of curcumin analogues in rats" Agents and Actions, vol. 12.4 (1982).

Huang, et al., (1992) "Inhibitory by benzo[a]pyrene and 7,12-dimethylbenz[a]anthracene" Carcinogenesis vol. 13 No. 11, pp. 2183–2186.

Donatus, et al., (1990) "Cytotoxic and cytoprotective activities of curcumin", Biochemical Pharmacology, vol. 39, No. 12, pp. 1869–1875.

Conney et al., "Inhibitory effect of curcumin and some related dietary componds on tumor promotion and arachidonic acid metabolism in mouse skin" Adv. Enz. Reg. 31:385.

Starr, O., (1994) Inform "Use supplements to help heal injuries", VeloNews Aug. 8, 1994.

Hasegawa, T. "Anti-Stress Effect of $\beta$-Carotene", Ann. N.Y. Acad. Sci.

Advertisement for Oxi-pro Anti-oxidant by Champion Nutrition (1993).

Advertisement for Centrum, Lederle Consumer Health (1993).

Advertisement for Choline Cocktail, Twinlab Specialty Corporation (1994).

Booklet for Powerbar by Powerfood Inc., (1993).

Article from Medical Tribune (1992) Circle No. 53 of Reader Service Card.

Article by Wholefoods (Aug., 1994), Circle No. 40 and 41 of Reader Service Card.

HEALTH FOOD PRODUCT AND ITS USES

FIELD OF THE INVENTION

The present invention relates to the design and manufacture of a health food product which contains an edible first component containing an antioxidant, and an edible second component containing a carbohydrate and/or a fat and/or a protein. The first component is in the form of a discrete portion from the second component to protect the first component, to maximize absorption of the first component in the gastrointestinal tract and/or to provide a product having advantageous shelf-life and appearance.

The present invention also relates to a unique blend of antioxidant compounds which, upon consumption, increases in vivo oxidant defense indices and prevents or attenuates in vivo exercise-mediated oxidative stress as measured by cellular and/or tissue damage.

BACKGROUND OF THE INVENTION

Several publications are referenced in this application within parentheses. Full citation to these references is found at the end of the specification immediately preceding the claims. These references describe the state of the art to which this invention pertains, and are incorporated herein by reference.

The consumption of foods rich in antioxidant compounds is well-known to be inversely correlated with the incidence of many chronic disease states (Halliwell, 1994; Thomas, 1994; Ziegler, 1989). Intake of certain of these compounds, such as vitamins C, E and A, is in fact essential for human life. However, most of the natural compounds present in food possessing antioxidant potential are currently considered to be "non-nutritive". Given the preponderant accumulation of epidemiological data and increasing amount of mechanistic data which support an important role for antioxidants in the maintenance of long-term health, their status as "non-nutritive" food components may have to be reconsidered in the future.

The importance of oxidant defense systems in humans is demonstrated by the essential in vivo presence of both enzymatic as well as non-enzymatic antioxidant components (Thomas, 1994). Oxidative stress and resultant oxidative damage may occur as a result of oxidative insults such as air pollution or the "oxidative burst" characteristic of activated neutrophils mediated by the immune response. A constant source of oxidative stress results from formation of superoxide anion via "electron leakage" in the mitochondria during production of adenosine triphosphate (ATP). Although superoxide anion is not exceedingly reactive in and of itself, it can initiate a chain of events that eventually results in the formation of the highly reactive free radicals and other oxidants. If these reactive oxygen species are not controlled by enzymatic and/or non-enzymatic antioxidant systems, in vivo oxidation of critical cellular components such as membranes, DNA and proteins will result, eventually leading to tissue damage and dysfunction.

Intense exercise can contribute significantly to oxidative stress in a number of ways. Most individuals have at some time in their lives experienced soreness and fatigue after physical exertion. For individuals that desire intense, frequent exercising, the effects of oxidative stress can often inhibit the intensity and/or reduce the frequency of workout routines.

Intense exercise results in a number of physiological changes in the body. First, aerobic respiration is dramatically increased, thereby increasing superoxide anion generation as much as 10-fold or more (Halliwell, 1994) in addition to increasing exposure to environmental oxidative insults such as air pollution. Second, muscle and joint inflammation often result from intense exercise, thus triggering tissue infiltration of neutrophils and subsequent release of reactive oxygen species during the "oxidative burst".

It would therefore be desirable to provide a shelf-stable, visually appealing and flavorful food product comprising carbohydrate and/or fat and/or protein, and other nutritive and non-nutritive compounds, that provides energy and alleviates the effects of oxidative stress and other damage resulting from intense exercise.

The following references, each of which are also incorporated herein by reference, further disclose the state of the art.

U.S. Pat. No. 4,451,488 to Cooke et al. discloses a shelf-stable, intermediate moisture, food bar having a soft and chewy texture, and low sugar content formed from a combination of at least two polyhydric alcohols in varying ratios, one of which comprises a sugar alcohol and the other either glycerol or propylene glycol (abstract). The food bar may additionally contain a mixture of dry ingredients selected from the group consisting of grains, fruits, nuts, chocolate chips and vegetables (column 3, lines 51–57).

U.S. Pat. No. 5,290,605 to Shapira discloses a nutritional soft drink for protecting against the danger of exposure to UV light comprising a mixture of carotenoids, optionally together with vitamin C and/or vitamin E and/or other physiologically acceptable antioxidants (abstract).

U.S. Pat. No. 5,234,702 to Katz discloses the incorporation of an antioxidant system of natural ingredients to minimize the oxidation of a powdered nutritional product (abstract). The antioxidant system is made up of ascorbyl palmitate, beta carotene and/or mixed tocopherols, and citrate (abstract and column 2, lines 56–59).

OBJECTS OF THE INVENTION

It is an object of the present invention to provide a food product comprising a unique blend of antioxidant components that enhance in vivo oxidant defense indices and reduce in vivo oxidant stress and damage resulting from intense exercise.

Further, it is an object of this invention to provide a food product that overcomes the food product development drawbacks of certain of the incorporated antioxidants; those drawbacks including disadvantageous yellow/orange color and chemical instability of the antioxidant blend to heat, light and oxygen (Schmitz et al., 1993; Encyclopedia of Food Science and Technology, 1991).

It is another object of the present invention to provide a food product with improved taste that maximizes absorption in the gastrointestinal tract of fat-soluble antioxidant components via localization within a lipid-based carrier formed within the food product.

SUMMARY OF THE INVENTION

The present invention relates to a food product which comprises a first component and a second component, wherein the first component is in the form of a discrete portion from the second component. The first component comprises an antioxidant, preferably an antioxidant blend, in addition to a carbohydrate and/or fat and/or protein, and other nutritive and non-nutritive compounds. The second component comprises a carbohydrate and/or fat and/or protein, and other nutritive and non-nutritive compounds. The product delivers nutritive and non-nutritive compounds which improve the antioxidant defense system and reduce the occurrence of cellular damage secondary to exercise associated oxidative damage in humans.

Advantageously, the antioxidant blend comprises at least two antioxidants selected from the group consisting of curcumin, all-trans beta-carotene, cis beta-carotenes, all-trans alpha-carotene, cis alpha-carotenes, all-trans lycopene, cis lycopenes, all-trans gamma-carotene, cis gamma-carotenes, zeta-carotene, phytofluene, phytoene, vitamin C and vitamin E. The first component may also contain an antiinflammatory agent, for example a tumeric extract such as curcumin.

Advantageously, the antioxidants are concentrated in a core or discrete portion within the food product to provide protection from heat, light and oxygen and also to avoid disadvantageous coloration of the food product by the antioxidants. Preferably, the antioxidants are localized in a lipid-based carrier within the food product to promote absorption and digestion of the carotenoid blend and curcumin.

The present invention provides a method of increasing in vivo oxidant defense indices in an animal by administering a food product of the invention in an amount effective for increasing in vivo oxidant defense indices, and a method of attenuating in vivo exercise-mediated oxidative stress in an animal by administering a food product of the invention in an amount effective for attenuating in vivo exercise mediated oxidative stress.

Additional objects, advantages and features of the various aspects of the present invention will become apparent from the following description of its preferred embodiments, such description being given in conjunction with the accompanying drawings.

DETAILED DESCRIPTION OF THE INVENTION

Figure 1:
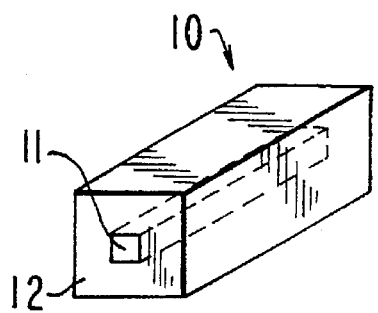
FIG. 1 illustrates a perspective view of a food product in accordance with a preferred embodiment of the present invention containing a first component in the form of an internalized core within the second component.

Referring initially to FIG. 1, a food product 10 is illustrated that includes an internalized core of first component 11 within second component 12.

Figure 2:
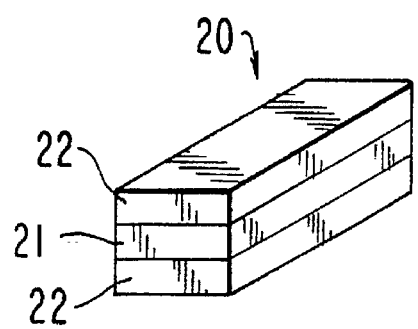
FIG. 2 illustrates a perspective view of a food product in accordance with a preferred embodiment of the present invention containing a first component in the form of a sandwich layer between the second component.

FIG. 2 illustrates a food product 20 that includes a layer of first component 21 sandwiched between second component 22.

Figure 3:
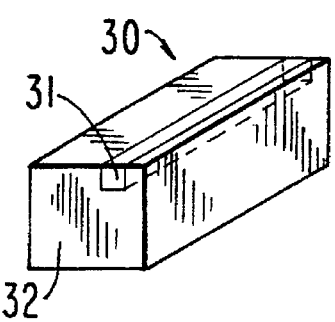
FIG. 3 illustrates a perspective view of a food product in accordance with a preferred embodiment of the present invention containing a first component in the form of a strip on the second component.

FIG. 3 illustrates a food product 30 that includes a strip of first component 31 on second component 32.

Figure 4:
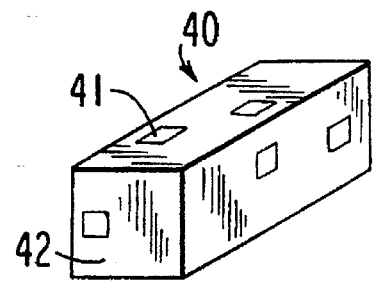
FIG. 4 illustrates a perspective view of a food product in accordance with a preferred embodiment of the present invention containing a first component in the form of discrete chunks within the second component.

FIG. 4 illustrates a food product 40 that includes discrete chunks of first component 41 within second component 42.

Figure 5:
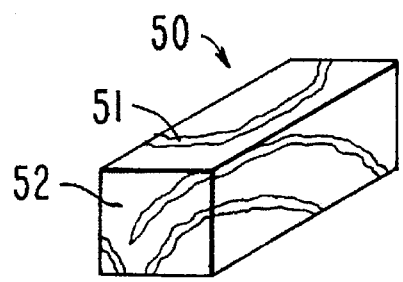
FIG. 5 illustrates a perspective view of a food product in accordance with a preferred embodiment of the present invention containing a first component mixed with the second component to form random discrete striations within a marbleized product.

FIG. 5 illustrates a food product 50 that includes a first component 51 mixed with a second component 52 to form random discrete striations within a marbleized product.

It should be appreciated that the food products illustrated in the figures can be in any convenient size and shape, including individual bite-sized pieces and other conventional confectionery food product sizes in square, rectangular, round, oval, spherical, elliptical, donut or other shapes. For the first component to form a discrete portion from the second component, the second component is advantageously solid or semi-solid and the first component is solid, semi-solid, a gel or a liquid.

It should be understood that the blend of antioxidant components described herein is chemically unstable toward excessive heat, light and oxygen. Upon exposure of this blend to excessive amounts of heat, light and/or oxygen, a loss of in vivo biological antioxidant activity will ensue. Thus, it is preferable to protect the antioxidant blend from heat, light and/or oxygen.

It should be further understood that absorption in the gastrointestinal tract of the fat-soluble components of said antioxidant blend is enhanced by the presence of adequate fat in the product and is further enhanced by direct incorporation into a lipid matrix within the food product. Advantageously, the absorption in the gastrointestinal tract of the fat-soluble components of the first component is enhanced by incorporating the first component into a lipid matrix separate from the second component while maintaining a product having a total fat content of preferably about 2% to about 40% by weight, more preferably about 2 to about 30 wt. %, even more preferably about 2 to about 20 wt. % and most preferably about 2 to about 15 wt. %. Incorporating the first component in a lipid portion that is separate from the second component provides for enhanced absorption without greatly increasing the overall fat content of the food product.

Finally, it should be appreciated that the distinctive yellow/orange pigmentation of certain of the biologically active compounds in the stated antioxidant blend is disadvantageous with respect to consumer visual appeal with the production of flavored products typically not associated with a yellow/orange color, including but not limited to banana, berry and chocolate flavors. Concentration of said pigments within a discrete portion, such as an internalized core, a layer, a strip, a chunk or marbleized striations, during manufacture of the product overcomes this problem. In this manner, the chemically unstable antioxidants are protected from heat, light and/or oxygen by being at least partially surrounded by the second component.

In addition, by maintaining the first component in the form of a discrete portion from the second component, the distinctive yellow/orange pigmentation of certain of the biologically active ingredients in the first component does not discolor the second component. This provides a food product with advantageous shelf-life and consumer visual appeal.

The first component comprises an antioxidant, preferably an antioxidant blend, and may further comprise a carbohydrate and/or fat and/or protein, and other nutritive and non-nutritive compounds. Advantageously, the antioxidant blend comprises at least two antioxidants selected from the group consisting of curcumin, all-trans beta-carotene, cis beta-carotenes, all-trans alpha-carotene, cis alpha-carotenes, all-trans lycopene, cis lycopenes, all-trans gamma-carotene, cis gamma-carotenes, zeta-carotene, phytofluene, phytoene, vitamin C and vitamin E.

The first component may further comprise an antiinflammatory agent, advantageously a turmeric extract such as curcumin.

Preferably, the antioxidant is a nutritive antioxidant, and the antioxidant blend contains at least two nutritive antioxidants. The antioxidant blend may further contain a non-nutritive antioxidant.

Advantageously, the nutritive antioxidants are selected from the group consisting of provitamin A carotenes (including all-trans beta-carotene and cis beta-carotenes, all-trans alpha-carotene and cis alpha-carotenes, all-trans gamma-carotene and cis gamma-carotenes), vitamin C and vitamin E, and the non-nutritive antioxidants are selected from the group consisting of non-provitamin A carotenes (zeta-carotene, all-trans lycopene, cis lycopenes, phytofluene, phytoene, and curcumin) and an antiinflammatory agent.

The first component may further contain a lipid, for example long-chain saturated or unsaturated mono-, di- or tri-acylglycerols or medium-chain saturated or unsaturated mono-, di-, or tri-acylglycerols. Preferably, the first component comprises a lipid-based carrier to promote absorption of the lipid-soluble antioxidants in the gastrointestinal tract.

Preferably, the amount of antioxidants in the lipid-based carrier is about 10 to about 90 wt. %, more preferably about 15 to about 80 wt. %, even more preferably about 20 to about 70 wt. %, and most preferably about 30 to about 60 wt. % of the lipid-based carrier.

The first component may further contain an additional nutritive compound, such as a mineral supplement and B vitamins, or an additional non-nutritive compound, such as ginkgo biloba extract, ginseng extract, green tea extract, licorice extract or any other herbal compounds and/or plant-based extracts.

The second component comprises a carbohydrate and/or fat and/or protein, and advantageously other nutritive and non-nutritive compounds, such as a mineral, a vitamin, herbal compounds and other plant-based extracts.

In accordance with the present invention, the first component is at least partially surrounded by the second component to protect the first component from heat, light and oxygen, to promote absorption of the first component and to provide a product having advantageous shelf-life and appearance.

The first component may be in the form of an internalized core within the second component, in the form of a sandwich layer between the second component, in the form of a strip on the second component, in the form of a discrete chunk in the second component or mixed with the second component to form random discrete striations of a marbleized product.

Preferably, the first component is present in an amount of about 5 to about 60 wt. % of the food product, more preferably about 5 to about 50 wt. %, even more preferably about 5 to about 40 wt. % and most preferably about 5 to about 30 wt. %.

Preferably, the antioxidants are about 0.01 to about 4.0 wt. % of the food product, more preferably about 0.05 to about 3.0 wt. %, even more preferably about 0.10 to about 2.0 wt. % and most preferably about 0.20 to about 1.0 wt. %.

The present invention provides a method of increasing in vivo oxidant defense indices in a human or animal by administering a food product of the invention, and a method of attenuating in vivo exercise-mediated oxidative stress in a human or animal by administering a food product of the invention.

The present invention is further described and illustrated in the following examples. Further objects of this invention, together with additional features contributing thereto and advantages accruing therefrom, will be apparent from the following examples of the invention. It will be appreciated that variations and modifications to the products and methods can be made by the skilled person without departing from the spirit or scope of the invention as defined in the appended claims.

EXAMPLE 1

Ingredients for the first component are blended in such a way that the antioxidant compounds are dispersed in the lipid-based carrier and then mixed with the remaining ingredients. The remaining ingredients or a portion thereof may or may not be concentrated, though temperature/time parameters should ensure efficacy of all nutrients used. Any of a number of batch or continuous mixers may be used; the resultant mixture advantageously contains a homogeneous mixture of antioxidant compounds. Ingredients for the second component or a portion thereof may or may not be concentrated, and are blended in such a way that the resultant mixture is well mixed. Any number of batch or continuous mixers may be used. The first and second components are metered through a co-extruder in such a way that the first component is delivered as an internalized core within the second component. Various co-extruder nozzle designs, and adjustment of component feed rates may be used to deliver dual component systems of various size, shape and component percentage. The product can be further shaped after discharge from the co-extruder and is cooled, cut to desired length dimension if necessary, and packaged.

EXAMPLE 2

Ingredients for the first component are blended in such a way that the antioxidant compounds are dispersed in the lipid-based carrier and then mixed with the remaining ingredients. The remaining ingredients or a portion thereof may or may not be concentrated, though temperature/time parameters should ensure efficacy of all nutrients used. Any of a number of batch or continuous mixers may be used; the resultant mixture advantageously contains a homogeneous mixture of antioxidant compounds. Ingredients for the second component or a portion thereof may or may not be concentrated, and are blended in such a way that the resultant mixture is well mixed. Any number of batch or continuous mixers may be used. The second component is metered into a slab of desired height via depositing rolls or other appropriate process. The first component is metered into a slab of desired height via depositing rolls or other appropriate process and deposited on top of the second component. The second component is then metered into a slab of desired height via depositing rolls or other appropriate process and deposited on top of the first component, forming a product consisting of the first component sandwiched between the second components. The slab may be cooled, cut to desired width and length, and packaged.

EXAMPLE 3

Ingredients for the first component are blended in such a way that the antioxidant compounds are dispersed in the lipid-based carrier and then mixed with the remaining ingredients. The remaining ingredients or a portion thereof may or may not be concentrated, though temperature/time parameters should ensure efficacy of all nutrients used. Any of a number of batch or continuous mixers may be used; the resultant mixture advantageously contains a homogeneous mixture of antioxidant compounds. Ingredients for the second component or a portion thereof may or may not be concentrated, and are blended in such a way that the resultant mixture is well mixed. Any number of batch or continuous mixers may be used. The first and second components are metered through a co-extruder in such a way that the first component is delivered as a strip on the second component. Various co-extruder nozzle designs, and adjustment of component feed rates are used to deliver dual component systems of various size, shape and component percentage. The product is cooled, cut to desired length dimension if necessary, and packaged. An alternative method would incorporate specially designed depositing rolls to deliver the second component in a slab with properly sized channel(s). An extruder is used to deposit the first component into the channels of the second component. The product is cooled, cut to desired length dimension if necessary, and packaged.

EXAMPLE 4

Ingredients for the first component are blended in such a way that the antioxidant compounds are dispersed in the lipid-based carrier and then mixed with the remaining ingredients. The remaining ingredients or a portion thereof may or may not be concentrated, though temperature/time parameters should ensure efficacy of all nutrients used. Any of a number of batch or continuous mixers may be used; the resultant mixture advantageously contains a homogeneous mixture of antioxidant compounds. Ingredients for the second component or a portion thereof may or may not be concentrated, and are blended in such a way that the resultant mixture is well mixed. Any number of batch or continuous mixers may be used. The first component is extruded and cut, or slabbed and cut to the desired particulate size and shape, and should be further processed to keep the particulates free-flowing. The first component is metered into the second component at a rate which delivers the desired weight ratios of the two. The mixing of the first and second components is gentle enough to insure that the first component remains a discreet particulate. The resultant mixture is metered into a slab of desired height via depositing rolls or other appropriate process. The slab may be cooled, cut to desired width and length, and packaged.

EXAMPLE 5

Ingredients for the first component are blended in such a way that the antioxidant compounds are dispersed in the lipid-based carrier and then mixed with the remaining ingredients. The remaining ingredients or a portion thereof may or may not be concentrated, though temperature/time parameters should ensure efficacy of all nutrients used. Any of a number of batch or continuous mixers may be used; the resultant mixture advantageously contains a homogeneous mixture of antioxidant compounds. Ingredients for the second component or a portion thereof may or may not be concentrated, and are blended in such a way that the resultant mixture is well mixed. Any number of batch or continuous mixers may be used. The first and second components are metered into another mixer which serves to "fold" the components together, creating random and discrete striations within the marbleized product matrix. The resultant mixture is metered into a slab of desired height via depositing rolls or other appropriate process. The slab may be cooled, cut to desired width and length, and packaged.

EXAMPLE 6

A health food product having the following formulation was prepared:

| Ingredients | Range %'s First Component | Range %'s Second Component |
| --- | --- | --- |
| Corn Syrup | 30–40% | 20–30% |
| Whey Protein Concentrate | 10–20% | 10–20% |
| Dehydrated Apples | — | 20–30% |
| Dehydrated Cranberries | — | 5–10% |
| Crystalline Fructose | 10–20% | — |
| Fig Paste | 5–10% | — |
| Dextrose | — | 5–10% |
| Maltodextrin | 10–20% | 5–10% |
| Liquid Fructose | 5–10% | 5–10% |
| Glycerin | 1–5% | 1–5% |
| Vegetable Oil | 1–5% | 1–5% |
| Turmeric Extract | 0.1–1.0% | — |
| Carotenoid Blend | 0.1–1.0% | — |
| Vit. E & C Premix | 1.5–3.5% | — |
| Calcium Carbonate | — | 2–4% |
| Mineral Premix | — | 2–4% |
| Flavor | — | 0.25–1.5% |
| Color | — | 0.10–1.0% |
| Malic Acid | — | 1–2% |

EXAMPLE 7

An experimental design incorporating 20 dedicated (20–25 miles/week) runners was developed to test clinically the efficacy of the unique blend of antioxidants comprising curcumin, all-trans beta-carotene, cis beta-carotenes, all-trans alpha-carotene, cis alpha-carotenes, all-trans lycopene, cis lycopenes, all-trans gamma-carotene, cis gamma-carotenes, zeta-carotene, phytofluene, phytoene, vitamin C and vitamin E. Each subject was screened for diet, drug use, supplement use and age. During the first 8 weeks, 10 subjects consumed a placebo bar while 10 subjects consumed the actual food bar described in Example 6 made by the procedure described in Example 1. Following an 8 week washout period, the 2 groups of subjects crossed over with respect to consumption of the placebo or actual food bar. Serum, urine and expired breath samples were collected at appropriate times. The following parameters were tested:

1. measurement of oxidant defense indices
    a. non-enzymatic oxidant defense indices present in serum (carotenoids, vitamin E, vitamin C, curcumin, glutathione)
    b. enzymatic oxidant defense indices present in serum (intracellular and extracellular superoxide dismutase, ceruloplasmin)
2. measurement of oxidative stress
    a. low density lipoprotein susceptibility to peroxidation
    b. carbonyls in expired breath
    c. protein carbonyls in serum
    d. serum and urinary lipoperoxides
    e. formation of DNA cross-link products
    f. non-enzymatic prostanoids
3. measurement of oxidative stress via inflammatory related processes
    a. thromboxane A2 production/platelet aggregation b. serum and urinary prostacyclin
c. eicosinoid synthesis
d. platelet lipoxygenase The data collected during the clinical experiment described above confirm that the food product containing the described blend of antioxidant compounds and nutrients increases in vivo oxidative defense indices and decreases in vivo oxidative stress.

As illustrated by the foregoing description and examples, the present invention has great application for the formulation of a wide variety of edible products. The present invention provides for edible products which, upon consumption, increase in vivo oxidant defense indices and prevent or attenuate in vivo exercise-mediated oxidative stress as measured by cellular and/or tissue damage, without detrimentally affecting the taste, texture and appearance of the product.

LITERATURE CITED

Halliwell, B. (1994) Free radicals and antioxidants: a personal view. Nutr. Rev. 52:253–265.

Schmitz, H. H., Poor, C. L., Gugger, E. T. and Erdman, J. W., Jr. (1993) Analysis of carotenoids in human and animal tissues. Meth. Enz. 214:102–116.

Thomas, J. A. (1994) Oxidative stress, oxidant defense, and dietary constituents. In "Modern Nutrition in Health and Disease" (eds. Shils, M. E., Olson, J. A. and Shike, M.), pp. 501–512, Lea and Febiger, Philadelphia.

Vitamins. (1991) In "Encyclopedia of food science and technology", parts 1–8, volume 4, John Wiley and Sons, Inc.

Ziegler, R. G. (1989) A review of epidemiologic evidence that carotenoids reduce the risk of cancer. J. Nutr. 119:116–122.

We claim:

1. An edible food product, which comprises
   (a) an edible first component containing an antioxidant having in vivo biological antioxidant activity and
   (b) an edible second component containing an ingredient selected from the group consisting of a carbohydrate, a fat and a protein, and combinations thereof, said second component positioned for protecting the in vivo biological antioxidant activity of the antioxidant in the first component,
   wherein the first component is in the form of a discrete portion from the second component, wherein the antioxidant is an antioxidant blend containing at least two nutritive antioxidants selected from the group consisting of all-trans beta-carotene, cis beta-carotenes, all-trans alpha-carotene, cis alpha-carotenes, all-trans gamma-carotene, cis gamma-carotenes, vitamin C and vitamin E, and wherein the antioxidant blend further contains a non-nutritive antioxidant selected from the group consisting of zeta-carotene, all-trans lycopene, cis lycopenes, phytofluene, phytoene and an antiinflammatory agent.

2. The food product of claim 1, wherein the antiinflammatory agent is a turmeric extract.

3. The food product of claim 2, wherein the turmeric extract is curcumin.

4. The food product of claim 1, wherein the first component further contains a lipid.

5. The food product of claim 4, wherein the lipid is long- or medium-chain saturated or unsaturated, mono-, di-, or tri-acylglycerols.

6. The food product of claim 1, wherein the first component further contains an ingredient selected from the group consisting of a carbohydrate, a fat and a protein, and combinations thereof.

7. The food product of claim 1, wherein the first component further contains an additional nutritive or non-nutritive compound, or mixtures thereof.

8. The food product of claim 7, wherein the additional nutritive compound is selected from the group consisting of a mineral supplement and B vitamins.

9. The food product of claim 7, wherein the additional non-nutritive compound is selected from the group consisting of herbal compounds and other plant-based extracts.

10. The food product of claim 1, wherein the second component further contains a compound selected from the group consisting of a mineral, a vitamin, a herbal compound and a plant-based extract.

11. The food product of claim 1, wherein the first component is at least partially surrounded by the second component to protect the first component from heat, light and oxygen.

12. The food product of claim 11, wherein the first component is in the form of an internalized core.

13. The food product of claim 11, wherein the first component is in the form of a layer.

14. The food product of claim 11, wherein the first component is in the form of a strip.

15. The food product of claim 11, wherein the first component is in the form of a chunk.

16. The food product of claim 11, wherein the first component is mixed with the second component to form random discrete striations of a marbleized product.

17. A method of increasing in vivo oxidant defense indices in an animal, which comprises administering to the animal a food product as defined in claim 1 in an amount effective for increasing in vivo oxidant defense indices in the animal.

18. A method of attenuating in vivo exercise-mediated oxidative stress in an animal, which comprises administering to the animal a food product as defined in claim 1 in an amount effective for attenuating in vivo exercise-mediated oxidative stress in the animal.

19. An edible food product, which comprises
    (a) an edible first component in a lipid/carbohydrate system containing at least one nutritive antioxidant selected from the group consisting of all-trans beta-carotene, cis beta-carotenes, all-trans alpha-carotene, cis alpha-carotenes, all-trans gamma-carotene, cis gamma-carotenes, vitamin C and vitamin E, and at least one non-nutritive antioxidant selected from a group consisting of zeta-carotene, all-trans lycopene, cis lycopenes, phytofluene, phytoene and an antiinflammatory agent,
    (b) an edible second component containing at least one ingredient selected from the group consisting of a carbohydrate, a mineral, a fat and a protein, and combinations thereof,
    wherein the first component is in the form of an internalized core portion discrete from the second component and at least partially surrounded by the second component to protect the first component from heat, light and oxygen.

20. The food product of claim 19, wherein the first component contains at least two nutritive antioxidants.

21. The food product of claim 19, wherein the antiinflammatory agent is a turmeric extract.

22. The food product of claim 21, wherein the turmeric extract is curcumin.

23. The food product of claim 19, wherein the lipid is long- or medium-chain saturated or unsaturated, mono-, di-, or tri-acylglycerols.

24. The food product of claim 19, wherein the first component further contains an additional non-nutritive compound selected from the group consisting of herbal compounds and other plant-based extracts.

25. The food product of claim 19, wherein the second component further contains a compound selected from the group consisting of a vitamin, a herbal compound and a plant-based extract.

* * * * *